United States Patent
Costello et al.

(10) Patent No.: US 7,385,089 B2
(45) Date of Patent: Jun. 10, 2008

(54) FLUOROCHEMICAL KETONE COMPOUNDS AND PROCESSES FOR THEIR USE

(75) Inventors: Michael G. Costello, Afton, MN (US); Richard M. Flynn, Mahtomedi, MN (US); Jay F. Schulz, Inver Grove Heights, MN (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/567,398

(22) Filed: Dec. 6, 2006

(65) Prior Publication Data

US 2007/0163710 A1  Jul. 19, 2007

Related U.S. Application Data

(63) Continuation of application No. 60/753,885, filed on Dec. 23, 2005.

(51) Int. Cl.
*C07C 49/173* (2006.01)
*C07C 43/00* (2006.01)
*C10M 107/34* (2006.01)
*C09K 5/04* (2006.01)

(52) U.S. Cl. .................... 568/413; 568/416; 568/674; 568/675; 508/579; 508/582; 252/67

(58) Field of Classification Search ............ None
See application file for complete search history.

(56) References Cited

U.S. PATENT DOCUMENTS

| 1,968,049 | A | 7/1934 | Midgley, Jr. et al. |
| 3,185,734 | A | 5/1965 | Fawcett et al. |
| 3,810,874 | A | 5/1974 | Mitsch et al. |
| 3,847,978 | A * | 11/1974 | Sianesi et al. ............ 562/577 |
| 3,903,012 | A | 9/1975 | Brandreth |
| 4,067,884 | A | 1/1978 | Martini |
| 4,169,807 | A | 10/1979 | Zuber |
| 5,023,009 | A | 6/1991 | Merchant |
| 5,104,034 | A | 4/1992 | Hansen et al. |
| 5,125,978 | A | 6/1992 | Flynn et al. |
| 5,182,342 | A | 1/1993 | Feiring et al. |
| 5,210,106 | A | 5/1993 | Dams et al. |
| 5,247,101 | A | 9/1993 | Takago et al. |
| 5,354,922 | A | 10/1994 | Marchionni et al. |
| 5,393,852 | A | 2/1995 | Ishibe et al. |
| 5,399,718 | A | 3/1995 | Costello et al. |
| 5,466,877 | A | 11/1995 | Moore |
| 5,539,008 | A | 7/1996 | Dams et al. |
| 5,750,797 | A | 5/1998 | Vitcak et al. |
| 5,827,446 | A | 10/1998 | Merchant et al. |
| 5,851,436 | A | 12/1998 | Merchant et al. |
| 5,925,611 | A | 7/1999 | Flynn et al. |
| 6,046,368 | A | 4/2000 | Lamanna et al. |
| 6,080,448 | A | 6/2000 | Leiner et al. |
| RE37,119 | E | 4/2001 | Sherwood |
| 6,374,907 | B1 | 4/2002 | Tousignant et al. |
| 6,394,107 | B1 | 5/2002 | Kesari et al. |
| 6,399,729 | B1 | 6/2002 | Farnham et al. |
| 6,403,149 | B1 | 6/2002 | Parent et al. |
| 6,423,673 | B1 | 7/2002 | Owens et al. |
| 6,478,979 | B1 | 11/2002 | Rivers et al. |
| 6,649,719 | B2 | 11/2003 | Moore et al. |
| 6,759,374 | B2 | 7/2004 | Milbrath et al. |
| 6,982,173 | B2 | 1/2006 | Marchionni et al. |
| 7,100,380 | B2 | 9/2006 | Brasz et al. |

FOREIGN PATENT DOCUMENTS

| DE | 1294949 | 5/1969 |
| EP | 0435062 | 8/1993 |
| EP | 1 440 993 | 7/2004 |
| FR | 2287432 | 5/1976 |
| JP | 10/109954 | 4/1998 |
| JP | 11/151401 | 6/1999 |
| JP | 2000/265197 | 9/2000 |
| WO | WO 93/24586 | 12/1993 |
| WO | WO 96/40834 | 12/1996 |

OTHER PUBLICATIONS

Chen et al. Perfluoro tertiary alcohols II. Synthesis of high molecular weight perfluorinated diketones, keto alcohols, and tertiary dialcohols. Journal of Fluorine Chemistry, 1992, vol. 59 (1), pp. 113-125.*

Takeshi Sako, Masahito Sato, Noriaki Nakazawa, and Masaru Oowa, "Critical Properties of Fluorinated Ethers", J. Chem. Eng. Data 1996, 41, 802-805.

Akira Sekiya et al., "The potential of hydrofluoroethers to replace CFCs, HCFCs and PFCs", Journal of Fluorine Chemistry 101 (2000) pp. 215-221.

D. Sianesi et al. in *Organofluorine Chemistry: Principles and Commercial Applications*, edited by R.E. Banks et al., Plenum Press, New York and London, (1994), p. 450.

Research Disclosure Article No. 40576, Hydrofluoroethers as Fluoromonomer Reaction Media, Jan. 1998, pp. 81-82.

* cited by examiner

*Primary Examiner*—Sikarl A. Witherspoon
(74) *Attorney, Agent, or Firm*—Lucy C. Weiss

(57) ABSTRACT

A fluorochemical ketone compound consists of two terminal, branched, independently fluoroalkylcarbonyl or perfluoroalkylcarbonyl groups and an intervening linear perfluoropolyether segment, each of the terminal groups optionally comprising at least one catenated heteroatom, and the perfluoropolyether segment consisting essentially of at least one tetrafluoroethyleneoxy moiety and, optionally, at least one difluoromethyleneoxy moiety, the moieties being randomly or non-randomly distributed within the perfluoropolyether segment.

24 Claims, No Drawings

FLUOROCHEMICAL KETONE COMPOUNDS AND PROCESSES FOR THEIR USE

STATEMENT OF PRIORITY

This application claims the priority of U.S. Provisional Application No. 60/753,885 filed Dec. 23, 2005, the contents of which are hereby incorporated by reference.

FIELD

This invention relates to fluorinated ketone compounds and perfluorinated ketone compounds and, in other aspects, to processes for their use.

BACKGROUND

Fluorochemical ketone compounds comprise a class of commercially valuable chemical compounds that exhibit a wide range of properties. The compounds as a class are neutral and, in some cases, are surprisingly inert, thermally stable, and hydrolytically stable. Such properties have made them useful as heat transfer agents, as lubricants, and even as fire extinguishing agents.

SUMMARY

Thus, we recognize that there exists an ongoing need for fluorochemical ketone compounds that can meet the performance requirements of a variety of different applications. For example, there is a continuing need for fluorochemical ketones having a variety of different boiling ranges, thermal and/or hydrolytic stabilities, viscosity characteristics, and molecular weights.

Briefly, in one aspect, this invention provides a fluorochemical ketone compound consisting of two terminal, branched, independently fluoroalkylcarbonyl or perfluoroalkylcarbonyl (preferably, perfluoroalkylcarbonyl) groups and an intervening linear perfluoropolyether segment, each of the terminal groups optionally comprising at least one catenated (that is, in-chain) heteroatom, and the perfluoropolyether segment consisting essentially of (preferably, consisting of) at least one tetrafluoroethyleneoxy moiety and, optionally, at least one difluoromethyleneoxy moiety, the moieties being randomly or non-randomly distributed within the perfluoropolyether segment. The branching of the terminal fluoroalkylcarbonyl or perfluoroalkylcarbonyl groups is preferably at the carbon atom of the group's fluoroalkyl or perfluoroalkyl moiety that is adjacent to the group's carbonyl moiety. Preferably, the perfluoropolyether segment consists essentially of (more preferably, consists of) at least one tetrafluoroethyleneoxy moiety and at least one difluoromethyleneoxy moiety.

It has been discovered that a versatile new class of normally liquid perfluoropolyether diketone compounds can be produced, for example, by the reaction of perfluoropolyether diacyl fluorides with perfluoroolefins such as hexafluoropropene (HFP). The resulting diketones can be used as intermediates in the preparation of hydrofluoroethers (HFEs) by alkylation or of diols by reduction.

In addition, the diketones of the invention can be used in a number of different applications including, for example, use as a solvent in coating deposition, as a cleaning or drying fluid, as a polymerization medium, as a biological specimen or document preservation medium, as a heat transfer agent (for example, as a testing fluid for electronic components), as a cell size regulator for use in foam blowing, as a heat transfer agent for use in vapor phase soldering, as a metal working agent in the cutting or forming of metals, and as oils for lubrication or in the preparation of lubricant greases (for example, by blending with a fluorochemical polymer ). At least some of the diketones exhibit unexpectedly low viscosities at low temperatures (for example, viscosities of about $75 \times 10^{-6}$ $m^2$/s at $-50°$ C.), making them particularly useful as heat transfer fluids; and at least some of the diketones show surprising resistance to hydrolysis, also making them especially useful in heat transfer applications. Thus, at least some embodiments of the invention meet the above-described, ongoing need for fluorochemical ketones that can meet the performance requirements of a variety of different applications.

In other aspects, this invention provides the following processes for using the fluorochemical ketone compounds of the invention:

A process for removing a contaminant (for example, an oil or grease, a particulate, or water) from an article comprising contacting the article with a composition comprising at least one fluorochemical ketone compound of the invention.

A process for preparing a foamed plastic comprising vaporizing a blowing agent mixture in the presence of at least one foamable polymer or the precursors of at least one foamable polymer, the blowing agent mixture comprising at least one fluorochemical ketone compound of the invention.

A process for vapor phase soldering comprising melting solder by immersing at least one component that comprises solder in a body of fluorochemical liquid vapor that comprises at least one fluorochemical ketone compound of the invention.

A process for transferring heat comprising transferring heat between a heat source and a heat sink through the use of a heat transfer agent comprising at least one fluorochemical ketone compound of the invention.

A process for depositing a coating on a substrate comprising applying to at least a portion of at least one surface of the substrate a composition comprising (a) a solvent composition comprising at least one fluorochemical ketone compound of the invention; and (b) at least one coating material (for example, a fluorochemical polyether or a document or specimen preservation material) that is soluble or dispersible in the solvent composition.

A process for metal, cermet, or composite working comprising applying a working fluid to a metal, cermet, or composite workpiece and tool, the working fluid comprising at least one fluorochemical ketone compound of the invention and at least one lubricious additive.

A polymerization process comprising polymerizing at least one monomer (preferably, a fluorine-containing monomer) in the presence of at least one polymerization initiator and at least one fluorochemical ketone compound of the invention.

In still other aspects, this invention also provides:

A hydrofluoroether compound produced by (a) reacting at least one fluorochemical ketone compound of the invention with at least one fluoride source to form at least one fluorochemical alkoxide; and (b) reacting the fluorochemical alkoxide with at least one alkylating agent to form at least one hydrofluoroether compound.

A perfluoropolyether diol produced by reacting at least one fluorochemical ketone compound of the invention with at least one reducing agent.

A composition comprising at least one fluorochemical ketone compound of the invention (preferably, having randomly distributed difluoromethyleneoxy and tetrafluoroethyleneoxy moieties).

DETAILED DESCRIPTION

Definitions

As used in this patent application:

"catenated heteroatom" means an atom other than carbon (for example, oxygen, nitrogen, or sulfur) that is bonded to carbon atoms in a carbon chain so as to form a carbon-heteroatom-carbon chain;

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"normally liquid" means liquid under ambient conditions of temperature and pressure (for example, at about 20° C. and about 1 atmosphere); and "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Fluorochemical Ketone Compounds

The novel diketone compounds of the invention consist of two terminal, branched, independently fluoroalkyl or perfluoroalkylcarbonyl (preferably, perfluoroalkylcarbonyl) groups and an intervening linear perfluoropolyether segment, each of the terminal groups optionally comprising at least one catenated (that is, in-chain) heteroatom, and the perfluoropolyether segment consisting essentially of (preferably, consisting of) at least one tetrafluoroethyleneoxy moiety ($-CF_2CF_2O-$) and, optionally, at least one difluoromethyleneoxy moiety ($-CF_2O-$), the moieties being randomly or non-randomly distributed within the perfluoropolyether segment. The linear perfluoropolyether segment "consists essentially of" the aforementioned perfluoroalkyleneoxy moieties, in that linear or branched hexafluoropropyleneoxy ($-CF_2CF_2CF_2O-$ or $-CF(CF_3)CF_2O-$) and/or linear octafluorobutyleneoxy ($-CF_2CF_2CF_2CF_2O-$) and/or branched tetrafluoroethyleneoxy ($-CF(CF_3)O-$) moieties can optionally also be present in small amounts (for example, up to about five percent of the total number of perfluoroalkyleneoxy units in the segment) as the only other possible component moieties of the segment (besides a requisite terminal difluoromethylene moiety). The branching of the terminal fluoroalkylcarbonyl or perfluoroalkylcarbonyl groups is preferably at the carbon atom of the group's fluoroalkyl or perfluoroalkyl moiety that is adjacent to the group's carbonyl moiety. Preferably, the perfluoropolyether segment consists essentially of (more preferably, consists of) at least one tetrafluoroethyleneoxy moiety and at least one difluoromethyleneoxy moiety.

A class of the compounds of the invention is that which can be represented by the following general formula (I):

$$R_f'-C(=O)-[CF_2-O-(CF_2CF_2O)_m-(CF_2O)_n-CF_2]-C(=O)-R_f'' \quad (I)$$

wherein $R_f'$ and $R_f''$ are each independently a branched perfluoroalkyl group that optionally contains at least one catenated heteroatom and that optionally comprises a terminal moiety selected from $-CF_2H$, $-CFHCF_3$, and $-CF_2OCH_3$; m is an integer of one to about 100; n is an integer of zero to about 100; and the tetrafluoroethyleneoxy ($-CF_2CF_2O-$) and difluoromethyleneoxy ($-CF_2O-$) moieties are randomly or non-randomly distributed. Preferably, $R_f'$ and $R_f''$ are each independently branched perfluoroalkyl groups that optionally contain at least one catenated heteroatom (more preferably, branched perfluoroalkyl groups having from about 3 to about 6 carbon atoms); m is an integer of one to about 25 (more preferably, one to about 15); and n is an integer of zero to about 25 (more preferably, zero to about 15).

Representative examples of the fluorochemical ketone compounds of the invention include the following:

$(CF_3)_2CFCOCF_2OCF_2OCF_2COCF(CF_3)_2$ $(CF_3)_2CFCOCF_2OC_2F_4OCF_2COCF(CF_3)_2$ $(CF_3)_2CFCOCF_2OCF_2OCF_2COCF(CF_3)_2$ $(CF_3)_2CFCOCF_2OC_2F_4OCF_2OCF_2COCF(CF_3)_2$ $(CF_3)_2CFCOCF_2OC_2F_4OC_2F_4OCF_2COCF(CF_3)_2$ $(CF_3)_2CFCOCF_2OC_2F_4OCF_2OCF_2OCF_2COCF(CF_3)_2$ $(CF_3)_2CFCOCF_2OCF_2OC_2F_4OCF_2OCF_2COCF(CF_3)_2$ $(CF_3)_2CFCOCF_2OC_2F_4OCF_2OC_2F_4OCF_2COCF(CF_3)_2$ $(CF_3)_2CFCOCF_2OC_2F_4OC_2F_4OCF_2OCF_2COCF(CF_3)_2$ $(CF_3)_2CFCOCF_2OC_2F_4OC_2F_4OC_2F_4OCF_2COCF(CF_3)_2$ $(CF_3)_2CFCOCF_2OC_2F_4OC_2F_4OC_2F_4OCF_2\\OCF_2COCF(CF_{32}$ $(CF_3)_2CFCOCF_2O(C_2F_4O)_m(CF_2O)_nCF_2COCF(CF_3)_2$, where m is an integer of 1-100 and n is an integer of 0-100

$C_3F_7O(CF_3)CFCOCF_2OCF_2OCF_2COCF(CF_3)OC_3F_7$ $C_3F_7O(CF_3)CFCOCF_2OC_2F_4OCF_2COCF(CF_3)OC_3F_7$ $C_4F_9O(CF_3)CFCOCF_2OCF_2OCF_2COCF(CF_3)OC_4F_9$ $C_3F_7OCF(CF_3)CF_2O(CF_3)CFCOCF_2OC_2F_4OCF_2OCF_2COCF(CF_3)OCF_2CF(CF_3)OC_3F_7$ $CF_3OC_3F_6O(CF_3)CFCOCF_2OC_2F_4OC_2F_4OCF_2COCF(CF_3)OC_3F_6OCF_3$ $C_3F_7O(CF_3)CFCOCF_2OC_2F_4OCF_2OCF_2OCF_2COCF(CF_3)OC_3F_7$ $H(CF_2)_4O(CF_3)CFCOCF_2OCF_2OC_2F_4OCF_2OCF_2COCF(CF_3)O(CF_2)_4CF_2H$ $HC_2F_4O(CF_3)CFCOCF_2OC_2F_4OCF_2OC_2F_4OCF_2COCF(CF_3)OC_2F_4CF_2H$ $(CF_3)_2CFCOCF_2OC_2F_4OC_2F_4OCF_2OCF_2COCF(CF_3)OC_3F_7$ $C_4F_9O(CF_3)CFCOCF_2OC_2F_4OC_2F_4OCF_2\\OCF_2COCF(CF_3)OC_4F_9$ $C_3F_7O(CF_3)CFCOCF_2OC_2F_4OC_2F_4OC_2F_4\\OCF_2COCF(CF_3)OC_3F_7$ $CF_3OC_3F_6OCF(CF_3)COCF_2O(C_2F_4O)_m(CF_2O)_n$
$CF_2COCF(CF_3) OC_3F_6OCF_3$, when m is an
integer of 1-100 and n is an integer of 0-100

$CF_3OC_3F_6OCF(CF_3)COCF_2OC_2F_4OCF_2COCF(CF_3)$
$OC_3F_6OCF_3$ $CF_3OC_3F_6OCF(CF_3)COCF_2O(C_2F_4O)_2CF_2COCF$
$(CF_3)OC_3F_6OCF_3$.

and the like, and mixtures thereof. Of such compounds (as well as others in general), preferred compounds have no hydrogen in the terminal groups (that is, the terminal groups are perfluorinated), and more preferred compounds have neither hydrogen nor catenated heteroatom(s) in the terminal groups.

The fluorochemical ketone compounds of the invention are hydrophobic and oleophobic, relatively chemically unreactive, relatively hydrolytically stable, thermally stable, water insoluble, and normally liquid (for example, at 20° C.), and they can be made in high yield, high functional group (that is, ketone group) purity, and with a wide range of molecular weights. For some applications, the compounds can be useful in the form of mixtures of compounds having varying numbers of the tetrafluoroethyleneoxy and difluoromethyleneoxy moieties and having boiling points within a narrow range such that the compounds in the mixture are essentially inseparable by distillation and have similar physical properties (for example, similar viscosities).

Preparation of Fluorochemical Ketone Compounds

The perfluoropolyether diketone compounds of the invention can be prepared from the corresponding perfluoropolyether diacyl fluorides by combining at least one perfluoropolyether diacyl fluoride with at least one perfluoroolefin (for example, hexafluoropropene), perfluorovinyl ether, or fluorovinyl ether (preferably, at least from a cost perspective, a perfluoroolefin) in the presence of at least one anhydrous fluoride source (for example, anhydrous potassium fluoride) and at least one anhydrous, polar, aprotic solvent (for example, diglyme (that is, diethylene glycol dimethyl ether or bis(2-methoxy)ethyl ether)). A phase transfer catalyst can be utilized, if desired.

For example, a perfluoropolyether diacyl fluoride, an anhydrous fluoride source (generally a catalytic amount), a solvent, and, optionally, a phase transfer catalyst (generally a catalytic amount) can be combined in any order in any suitable reactor (for example, a metal reactor; preferably, a pressure reactor), which can then be sealed and heated to a desired reaction temperature (for example, about 75° C.) under autogenous pressure. At least a stoichiometric amount (up to a stoichiometric excess of one hundred percent or more) of perfluoroolefin, perfluorovinyl ether, or fluorovinyl ether can then be added to the reactor (or can be added continuously or in portions), generally with stirring or agitation of the reactor contents and, preferably, with temperature control.

After completion of perfluoroolefin, perfluorovinyl ether, or fluorovinyl ether addition, or after the reaction has run to completion, the reactor can be cooled and vented and the contents purified by any suitable separation method. For example, the resulting reaction mixture can be filtered (for example, to remove the fluoride source), phase separated (for example, to remove the solvent and catalyst), washed with a washing solvent (for example, washed with acetone to remove residual solvent and catalyst), phase separated (for example, to remove the washing solvent), and subjected to rotary evaporation and/or distillation (for example, to remove any residual volatile materials and to purify the resulting diketone product).

The perfluoropolyether diacyl fluorides can be prepared by the photooxidative polymerization of tetrafluoroethylene (TFE), which results in the formation of perfluoropolyether polyperoxides. The perfluoropolyether polyperoxides can be reduced by physical techniques (for example, thermal or photochemical treatment) or by chemical techniques (for example, reduction with hydrogen in the presence of noble metal catalysts such as platinum or palladium). The reduction breaks the peroxidic perfluoropolyether bonds and can give perfluoropolyethers of lower molecular weight having —COF end groups and randomly-distributed difluoromethyleneoxy and tetrafluoroethyleneoxy moieties. This synthetic method is described in more detail, for example, in U.S. Patent Application Publication No. 2003/0013923 A1 (Marchionni et al.) and in U.S. Pat. No. 5,354,922 (Marchionni et al.), the descriptions of which are incorporated herein by reference.

Alternatively, the perfluoropolyether diacyl fluorides can also be prepared by decomposition of α,ω-dihydroperfluoropolyethers with antimony pentafluoride (for example, essentially as described in Example 7 of U.S. Pat. No. 6,046,368 (Lamanna et al.)); by fluorination, using fluorine gas, of α,ω-perfluoropolyether dimethyl esters and subsequent treatment with, for example, a catalytic amount of pyridine (for example, essentially as described in U.S. Pat. No. 5,399,718 (Costello et al.) and U.S. Pat. No. 5,466,877 (Moore), respectively); or by fluorination, using fluorine gas, of hydrocarbon polyether diesters and subsequent treatment with, for example, a catalytic amount of pyridine (for example, essentially as described in U.S. Pat. No. 5,399,718 (Costello et al.) and U.S. Pat. No. 5,466,877 (Moore), respectively). These methods can provide materials having randomly or non-randomly distributed difluoromethyleneoxy and tetrafluoroethyleneoxy moieties, depending upon the nature of the starting perfluoropolyether.

Perfluoroolefins that are useful in carrying out the preparation process include those that contain at least one carbon atom bonded to one of the carbon atoms of the olefinic double bond. Such perfluoroolefins provide product fluorochemical ketone compounds that are generally characterized by the presence of terminal branched perfluoroalkylcarbonyl groups.

The perfluoroolefins can be prepared by any of a variety of standard synthetic procedures that are well-known in the art. Some perfluoroolefins (for example, $CF_3CF=CF_2$, $C_5F_{11}CF=CF_2$, and $C_2F_5CF=CF_2$) are also commercially available (for example, from Synquest or from Apollo Scientific, Ltd.).

Representative examples of perfluoroolefins that are useful in preparing the fluorochemical ketone compounds include $CF_3CF=CF_2$, $C_3F_7CF=CF_2$, $C_5F_{11}CF=CF_2$, $CF_3CF_2CF=CF_2$, and the like, and mixtures thereof (Mixtures can be used, if desired, but mixtures are generally less preferred due to the resulting production of product mixtures that can require purification.) Preferred perfluoroolefins include $CF_3CF=CF_2$, $C_2F_5CF=CF_2$, and mixtures thereof $CF_3CF=CF_2$ is more preferred.

Fluoro- and perfluorovinyl ethers that are useful in carrying out the preparation process include those that possess a terminal perfluorovinyl group. Such fluoro- and perfluorovinyl ether starting compounds, which optionally can further contain one or more catenated heteroatoms (in addition to the ether oxygen of the fluoro- and perfluorovinyl ethers), can be prepared by the reaction of a fluorochemical acid fluoride or a fluorochemical ketone with hexafluoropropylene oxide (HFPO) to form an intermediate branched acid fluoride adduct. This adduct can then be reacted with a base to form an intermediate carboxylic acid salt, which can then be decarboxylated at elevated temperature (optionally, in the presence of an inert solvent). Some perfluorovinyl ethers (for example, perfluorovinyl ethers such as $C_3F_7OCF=CF_2$, $C_3F_7OCF(CF_3)CF_2OCF=CF_2$, and $CF_3OCF=CF_2$) are also commercially available (for example, from Synquest or from Apollo Scientific, Ltd.).

Representative examples of fluoro- and perfluorovinyl ethers that are useful in preparing the fluorochemical ketone compounds of the invention include $C_3F_7OCF=CF_2$, $C_3F_7OCF(CF_3)CF_2OCF=CF_2$, $CF_3OCF=CF_2$, $C_4F_9OCF=CF_2$, $CF_3OC_3F_6OCF=CH_2$, $C_2F_5OCF=CF_2$, $(CF_3)_2CFCF_2OCF=CF_2$, $C_5F_{11}OCF=CF_2$, $HCF_2CF_2CF_2OCF=CF_2$, $CH_3OCF_2CF_2CF_2OCF=CF_2$, $CF_3CFHCF_2CF_2OCF=CF_2$,

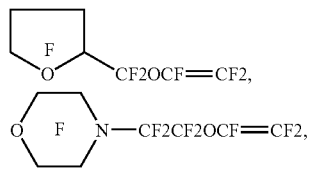

and the like, and mixtures thereof. Preferred vinyl ethers include $C_3F_7OCF=CF_2$, $C_4F_9OCF=CF_2$, $CF_3OC_3F_6OCF=CF_2$, and mixtures thereof $C_3F_7OCF=CF_2$, $C_4F_9OCF=CF_2$, and mixtures thereof are more preferred. (Mixtures of starting compounds can be used, if desired, but mixtures are generally less preferred due to the resulting production of product mixtures that can require purification.)

Suitable anhydrous fluoride sources include anhydrous fluorine-containing compounds that can dissociate to provide an anhydrous source of fluoride ion. Such compounds include metal fluorides (for example, potassium fluoride, rubidium fluoride, cesium fluoride, and the like, and mixtures thereof), metal bifluorides, quaternary ammonium fluorides, quaternary phophonium fluorides, and the like, and mixtures thereof. Preferred anhydrous fluoride sources include potassium fluoride, cesium fluoride, and mixtures thereof, with potassium fluoride being more preferred.

Suitable solvents for use in carrying out the preparation process include anhydrous, polar, aprotic solvents such as glycol ether solvents (for example, glyme, diglyme, triglyme, tetraglyme, and the like, and mixtures thereof), tetrahydrofuran, dimethylformamide, dimethyl sulfoxide, sulfolane, acetonitrile, and the like, and mixtures thereof. Preferred solvents include glyme, diglyme, triglyme, tetraglyme, dimethylformamide, and mixtures thereof, with glyme, diglyme, dimethylformamide, and mixtures thereof being more preferred and diglyme most preferred.

Suitable phase transfer catalysts include quaternary ammonium salts, quaternary phosphonium salts, crown ethers, cryptands, and the like, and mixtures thereof. Preferred salt counter ions include those that are commercially available (for example, chloride), as well as those such as monoalkyl sulfates, monoalkyl sulfonates, and the like, and mixtures thereof. Useful crown ethers include 4'-aminobenzyl-15-crown-5, 1-aza-12-crown-5, 1-aza-15-crown-5, 1-aza-18-crown-5, bis[(benzo-15-crown-5)-15-ylmethyl]pimelate, dicyclohexano-18-crown-6, 4'-formylbenzo-15-crown-5, 2-(hydroxymethyl)-15-crown-5, 4'-nitrobenzo-15-crown-5, poly[(dibenzo-18-crown-6)-coformaldehyde], and the like, and mixtures thereof. Useful commercially available cryptands include KRYPTOFIX 21, 211, 222, and 222b (available from Sigma-Aldrich Chemical Company, Milwaukee, Wis.). Preferred catalysts are quaternary ammonium salts, due to their relative abundance and cost effectiveness. Useful commercially available quaternary ammonium salts include ADOGEN 464 (a methyltrialkyl ($C_8$-$C_{10}$) ammonium chloride available from Sigma-Aldrich Chemical Company). Another preferred phase transfer catalyst is $(C_8H_{17})_3N^+CH_3^-OSO_3CH_3$, which can be prepared by reaction of trioctylamine with dimethylsulfate. If utilized, phase transfer catalyst is typically added at a concentration constituting between about 0.001 mol percent and about 5.0 mol percent of the reaction mixture.

Use of Fluorochemical Ketone Compounds

The fluorochemical ketone compounds of the invention (or a normally liquid composition comprising, consisting, or consisting essentially thereof) can be used in various applications. For example, the compounds can be used as solvents for precision or metal cleaning of electronic articles such as disks or circuit boards; as heat transfer agents; as cell size regulators in making foam insulation (for example, polyurethane, phenolic, and thermoplastic foams); as carrier fluids or solvents for document or specimen preservation materials and for lubricants; as power cycle working fluids such as for heat pumps; as inert media for polymerization reactions; as buffing abrasive agents to remove buffing abrasive compounds from polished surfaces such as metal; as displacement drying agents for removing water, such as from jewelry or metal parts; as resist developers in conventional circuit manufacturing techniques including chlorine-type developing agents; and as strippers for photoresists when used with, for example, a chlorohydrocarbon such as 1,1,1-trichloroethane or trichloroethylene.

The fluorochemical ketone compounds typically exhibit high dielectric strengths (for example, greater than about $10^8$ ohm-cm), which can make them well-suited for use in the semiconductor industry. The fluorochemical ketone compounds (for example, those of Example 2 below) that exhibit unexpectedly low viscosities at low temperatures (for example, about $75 \times 10^{-6}$ m$^2$/s at $-50°$ C.) can be particularly useful in low temperature applications such as in heat transfer applications in the semiconductor, chemical processing, and pharmaceutical industries.

The fluorochemical ketone compounds can be used alone or in admixture with each other or with other commonly-used solvents (for example, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents are preferably at least partially fluorinated, can be chosen to modify or enhance the properties of a composition for a particular use, and can be utilized in ratios (of co-solvent(s) to fluorochemical ketone(s)) such that the resulting composition preferably has no flash point. If desired, the fluorochemical ketone compounds can be used in combination with other compounds that are very similar in properties relative to a particular use (for example, other fluorochemical ketone compounds) to form compositions that "consist essentially" of the fluorochemical ketone compounds of the invention.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The fluorochemical ketone compounds are useful as solvents for cleaning and drying applications such as, for example, those described in U.S. Pat. Nos. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.) the descriptions of which are incorporated herein. Both organic and inorganic substrates can be cleaned by contacting them with a composition comprising at least one fluorochemical ketone of the invention. Most contaminants can be removed, including hydrocarbon contaminants, fluorocarbon contaminants, particulates, and water.

In using the compounds for the drying of or displacing water from the surface of articles (such as circuit boards), the process of drying or water displacement described in, for example, U.S. Pat. No. 5,125,978 (Flynn et al.) can be used. Broadly, such process comprises contacting the surface of an article with a liquid composition comprising at least one fluorochemical ketone compound of the invention, preferably in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978 (Flynn et al.), which description is incorporated herein.

In using the compounds of the invention in vapor phase soldering, the process described in, for example, U.S. Pat. No. 5,104,034 (Hansen) can be used, which description is incorporated herein. Briefly, such process comprises immersing a component to be soldered in a body of vapor comprising at least one fluorochemical ketone compound of this invention to melt the solder. In carrying out such a process, a liquid pool of a fluorochemical ketone composition is heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the compounds of the invention as cell size regulators in making plastic foam (such as foamed polyurethane), the process reactants and reaction conditions described in, for example, U.S. Pat. Nos. 5,210,106 (Dams et al.) and U.S. Pat. No. 5,539,008 (Dams et al.) can be used, which descriptions are incorporated herein. One such process comprises vaporizing a blowing agent mixture in the presence of at least one foamable polymer or the precursors of at least one foamable polymer, the blowing agent mixture comprising at least one fluorochemical ketone compound of the invention.

In using the compounds of the invention as heat transfer agents, the processes described in, for example, U.S. Reissue Pat. No. 37,119 E (Sherwood) and U.S. Pat. No. 6,374,907 B1 (Tousignant et al.) can be used, which descriptions are incorporated herein. In carrying out such processes, heat is transferred between a heat source (for example, a silicon wafer or a component of a flat panel display) and a heat sink through the use of a heat transfer agent comprising at least one fluorochemical ketone compound of the invention. The fluorochemical ketones of the invention generally exhibit a wide liquid range, useful viscosity over that range, and relatively high thermal stability at end use temperatures, making them well-suited for use as heat transfer fluids.

In using the fluorochemical ketone compounds of the invention as deposition solvents in coating applications or in document or biological specimen preservation applications, the processes described in, for example, U.S. Pat. Nos. 5,925,611 (Flynn et al.) and U.S. Pat. No. 6,080,448 (Leiner et al.) can be used, which descriptions are incorporated herein. Such processes for depositing a coating on a substrate (for example, magnetic recording media or cellulose-based materials) comprises applying, to at least a portion of at least one surface of the substrate, a composition comprising (a) a solvent composition comprising at least one fluorochemical ketone compound of the invention; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Preferred materials include perfluoropolyether, hydrocarbon, and silicone lubricants; amorphous copolymers of tetrafluoroethylene; polytetrafluoroethylene; document preservation materials; specimen preservation materials; and combinations thereof. Most preferably, the material is a perfluoropolyether or a document or specimen preservation material.

In using the fluorochemical ketone compounds of the invention in cutting or abrasive working operations, the processes described in, for example, U.S. Pat. No. 6,759,374 (Milbrath et al.) can be used, the descriptions of which are incorporated herein. Such a process for metal, cermet, or composite working comprises applying a working fluid to a metal, cermet, or composite workpiece and tool, the working fluid comprising at least one fluorochemical ketone compound of the invention and at least one lubricious additive. The working fluid can further comprise one or more conventional additives (for example, corrosion inhibitors, anti-oxidants, defoamers, dyes, bactericides, freezing point depressants, metal deactivators, co-solvents, and the like, and mixtures thereof).

In using the fluorochemical ketone compounds of the invention as polymerization media or as chain transfer agents, the processes described in, for example, Research Disclosures, Number 40576, page 81 (January 1998) and in U.S. Pat. No. 5,182,342 (Feiring et al.) and U.S. Pat. No. 6,399,729 (Farnham et al.) can be used, the descriptions of which are incorporated herein. Such processes comprise polymerizing at least one monomer (preferably, at least one fluorine-containing monomer) in the presence of at least one polymerization initiator and at least one fluorochemical ketone compound of the invention.

The fluorochemical ketone compounds of the invention can also be used to prepare hydrofluoroether compounds (HFEs) by the alkylation of fluorochemical alkoxides prepared by the reaction of the fluorochemical ketone with an anhydrous alkali metal fluoride (for example, potassium fluoride or cesium fluoride) or anhydrous silver fluoride, preferably in an anhydrous polar, aprotic solvent. See, for example, the preparative methods described in French Patent Publication No. 2,287,432 and German Patent Publication No. 1,294,949, as well as the method described in detail in U.S. Pat. No. 5,750,797 (Vitcak et al.), the description of which is incorporated herein by reference.

Suitable alkylating agents for use in the preparation of the HFEs include dialkyl sulfates (for example, dimethyl sulfate), alkyl halides (for example, methyl iodide), alkyl p-toluenesulfonates (for example, methyl p-toluenesulfonate), alkyl perfluoroalkanesulfonates (for example, methyl perfluoromethanesulfonate), and the like, and mixtures thereof. Suitable polar, aprotic solvents include acyclic ethers such as diethyl ether, ethylene glycol dimethyl ether, and diethylene glycol dimethyl ether; carboxylic acid esters such as methyl formate, ethyl formate, and methyl acetate; carbonate esters such as diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and the like; and mixtures thereof.

Such reaction of the fluorochemical ketone compounds of the invention provides the corresponding hydrofluoroether compounds (that is, compounds consisting of two terminal alkoxy-substituted fluoroalkyl or perfluoroalkyl groups and the intervening linear perfluoropolyether segment of the fluorochemical ketone compound). Preferably, the alkyl moiety (which can be linear, branched, cyclic, or a combination thereof) of each terminal group of the HFE independently has from one to about 10 carbon atoms (more preferably, from one to about 3 carbon atoms).

The fluorochemical ketone compounds of the invention can also be used to prepare the corresponding perfluoropolyether diols (that is, compounds consisting of two terminal hydroxyl-substituted fluoroalkyl or perfluoroalkyl groups and the intervening linear perfluoropolyether segment of the fluorochemical ketone compound) by reaction with a reducing agent such as sodium borohydride, preferably in a polar aprotic solvent (for example, diglyme). The reaction can be carried out essentially as described at columns 11 and 12 of U.S. Pat. No. 6,649,719 (Moore et al.), the description of which is incorporated herein by reference. If desired, the diols can be further converted to the corresponding diacrylates (essentially as described at column 12 of the same reference, the description of which is also incorporated by reference herein) or reacted with isocyanates to form urethanes.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Test Methods

Nuclear Magnetic Resonance (NMR)

$^1$H and $^{19}$F NMR spectra were run on a Varian UNITYplus 400 Fourier transform NMR spectrometer (available from Varian NMR Instruments, Palo Alto, Calif.).

Gas Chromatography/Mass Spectroscopy (GCMS)

GCMS samples were run on, for example, a Finnigan TSQ7000 mass spectrometer (available from Thermo Electron Corporation, Waltham, Mass.).

Infrared (IR) Spectroscopy

IR spectra were run on a THERMO-NICOLET, Avatar 370 Fourier Transform Infrared (FTIR) Spectrometer (obtainable from Thermo Electron Corporation, Waltham, Mass.).

Viscosity Measurement

Kinematic viscosities were measured using Ubbelohde glass capillary viscometers (available from Cannon Instrument Co., State College, Pa.) and a SCHOTT AVS350 viscometer timer (available from Schott North America, Elmsford, N.Y.). Temperature was controlled using a Lawler temperature control bath (available from Lawler Manufacturing Company, Inc., Indianapolis, Ind.) filled with NOVEC-7500 (a hydrofluoroether; available from 3M Company, St. Paul, Minn.). The Lawler bath was cooled by a JULABO F-83 refrigerated circulator (available from Julabo USA, Allentown, Pa.).

Example 1

Preparation of $(CF_3)_2CFC(O)CF_2O(C_2F_4O)_m(CF_2O)_nCF_2C(O)CF(CF_3)_2$

A perfluoropolyether diacyl fluoride mixture was first prepared, essentially as described in Example 7 of U.S. Pat. No. 6,046,368 (Lamanna et al.). 76 g of H-GALDEN ZT 180 heat transfer fluid was added dropwise to a flask containing 1.8 g of $SbF_5$ (antimony pentafluoride, obtained from Sigma-Aldrich Chemical Company, Milwaukee, Wis.) over a period of about one hour. The heat transfer fluid, commercially available from Solvay-Solexis SpA, Bollate, Italy (Solvay-Solexis, Inc. Thorofare, N.J.) under the tradename H-GALDEN ZT 180, had the general formula $HCF_2O(C_2F_4O)_m(CF2O)_nCF_2H$ (with m and n varying independently) and a number average molecular weight as determined by nuclear magnetic resonance spectroscopy (NMR) of about 590. The heat transfer fluid contained at least seven discrete components, as determined by gas chromatography (GC). Subsequently, two additional charges of $SbF_5$ (1.8 g each) were added to the flask. Gas evolution, presumably $CF_3H$, was noted. After the final $SbF_5$ addition, the resulting mixture was stirred at room temperature for two hours, and 38 g of product diacyl fluorides were distilled directly from the mixture to a head temperature of 95° C. Infrared (IR) spectra of the resulting material showed the presence of the carbonyl absorbance band for a COF group at 1888.6 cm$^{-1}$. The material was a mixture of numerous perfluoropolyether diacyl fluorides.

The perfluoropolyether diacyl fluoride mixture (38 g) was combined with 260.4 g anhydrous diethylene glycol dimethyl ether ("diglyme"; obtained from Sigma-Aldrich Chemical Company, Milwaukee, Wis.), 5 g of spray-dried potassium fluoride (obtained from Sigma-Aldrich Chemical Company, Milwaukee, Wis., and further dried in an air oven at 120° C.), and 4.9 g of ADOGEN 464 phase transfer catalyst (a methyltrialkyl($C_8$-$C_{10}$) ammonium chloride obtained from Sigma-Aldrich Chemical Company, Milwaukee, Wis.; 49 percent by weight solution in anhydrous diglyme) in a 600 mL reactor (a pressure vessel or Parr reactor obtained from Parr Instrument Company, Moline, Ill.). The reactor was sealed and heated to 75° C. An excess (90 g) of hexafluoropropene (HFP; obtained from Dyneon, St. Paul, Minn.) was added to the reactor over a period of two hours in 10 g increments. After each 10 g addition of HFP, the pressure inside the reactor rose to about 3.06 atmospheres (45 psig) and decreased to less than 0.68 atmospheres (10 psig) within about 10 minutes. After HFP addition was completed, the reactor was stirred at 75° C. overnight. After the reactor was cooled to ambient temperature, it was opened, and the contents were filtered to remove the solid potassium fluoride catalyst. The resulting lower fluorochemical phase (110 g) was removed from the filtered reaction mixture using a separatory funnel. The resulting mixture was distilled using a concentric tube distillation column, and the fractions distilling from 24° C. to 108° C., which contained dimers of HFP, were discarded. Intermediate fractions distilling from 108° C. to 126° C. and from 126° C. to 174° C., which contained significant amounts of the trimers of HFP, were also discarded. The fraction distilling from 174° C. to 199° C. was analyzed by IR spectroscopy and by gas chromatography-mass spectrometry (GCMS). The IR spectrum of this fraction was consistent with a perfluoropolyether diketone structure (CO absorbance band at 1795 $cm^{-1}$, and no apparent CH absorbance bands were observed). The GCMS data showed the presence of several compounds of molecular weights consistent with the desired perfluoropolyether diketone structures. Further evidence for the diketone structures was obtained by $F^{19}$ NMR, which showed that the major components in the fraction were the desired diketones having a number average molecular weight of 734. The kinematic viscosity of the fraction distilling from 174° C. to 199° C. (that is, the diketone-containing fraction) was measured using an Ubbelohde 545-20 viscometer and a SCHOTT AS350 viscometer timer and was found to be $4.88 \times 10^{-6}$ $m^2/s$ (4.88 centistokes) at 0° C. and $77.29 \times 10^{-6}$ $m^2/s$ (77.29 centistokes) at −50° C.

Example 2

Preparation of $(CF_3)_2CFCF(OC_2H_5)CF_2O(C_2F_4O)_m(CF_2O)_nCF_2CF(OC_2H_5)CF(CF_3)_2$ 21.6 g of the diketone (the fraction boiling at greater than 174° C.) of Example 1, 152 g of diglyme (dried over 4A molecular sieves), 7.9 g anhydrous potassium fluoride, 4.1 g ADOGEN 464 phase transfer catalyst (49 percent by weight solution in anhydrous diglyme), and 19.0 g diethyl sulfate (obtained from Sigma-Aldrich Chemical Company, Milwaukee, Wis.) were placed in a 250 mL round bottom flask equipped with an overhead stirrer and a thermocouple. The resulting mixture was heated to 52° C. There was a brief exotherm up to about 72° C., after which the temperature was held at 52° C. for 60 hours. At the end of the 60 hours, 18 g of 45 percent by weight aqueous potassium hydroxide (obtained from Sigma-Aldrich Chemical Company, Milwaukee, Wis.) was added to the mixture, and the resulting mixture was further heated at 65° C. for two hours in order to hydrolyze the remaining diethyl sulfate. The resulting mixture was transferred to a larger flask with the addition of some water and was distilled using a Dean Stark trap to return the upper aqueous phase to the flask. The lower fluorochemical phase in the trap was separated (12.8 g), washed once with water, and analyzed by gas-liquid chromatography (GLC), IR spectroscopy, and gas chromatography-mass spectrometry (GCMS). The IR spectrum did not show carbonyl absorption and had a prominent complex of bands in the 2900-3000 $cm^{-1}$ region attributed to ethyl groups. The GLC results showed complete consumption of the starting diketones, with the formation of two sets of products. The main products (comprising about 86 percent by weight of the product mixture) were the desired bis(ethyl ether) product series, consistent with the GCMS analysis (which showed a series of bis(ethyl ethers) having a range of masses from 722 to 954).

Example 3

Preparation of $(CF_3)_2CFC(O)CF_2O(CF_2CF_2O)_2CF_2C(O)CF(CF_3)_2$ 111 g of $(FC(O)CF_2OCF_2CF_2)_2O$, 2.2 g anhydrous potassium fluoride, 0.23 g of ADOGEN 464 phase transfer catalyst, and 52 g of anhydrous diglyme were added to a clean, dry 600 mL reactor equipped with a stirrer, a heater, and a thermocouple. (The $FC(O)CF_2OCF_2CF_2)_2O$ was prepared by the direct fluorination of $(CH_3CO_2CH_2CH_2OCH_2CH_2)_2O$, essentially as described in U.S. Pat. No. 5,399,718 (Costello et. al.), to form a perfluorinated diester, which was converted to the corresponding diacyl fluoride, $(FC(O)CF_2OCF_2CF_2)_2O$, by reaction with a catalytic amount of pyridine, essentially as described in U.S. Pat. No. 5,466,877 (Moore).) The reactor was sealed, cooled to about −50° C. in dry ice, and 90 g of HFP was added. The reactor was removed from the dry ice and heated to a temperature of 125° C. over a period of 2.5 hours. The pressure in the reactor reached a maximum of 10.89 atmospheres (165 psig) and then decreased to 2.72 atmospheres (40 psig) after 2.5 hours. The reactor contents were allowed to cool, and excess pressure was vented. The reactor contents were added to a separatory funnel, and the lower phase (202.9 g) of the contents was isolated. The remaining upper phase was washed with a saturated sodium chloride solution, and the resulting lower phase (15.8 g) was combined with the aforementioned lower phase. This phase was washed with saturated sodium chloride solution, dried with anhydrous magnesium sulfate (obtained from Sigma-Aldrich Chemical Company, Milwaukee, Wis.), and fractionated under reduced pressure to provide 62.0 g of a fractionation cut boiling at 78-88° C. at 0.05 atmospheres (13 mm Hg). NMR analysis confirmed the structure of the fractionation cut as 96 mole percent pure 1,1,3,4,4,4-hexafluoro-1-{1,1,2,2-tetrafluoro-2-[1,1,2,2-tetrafluoro-2-(1,1,3,4,4,4-hexafluoro-2-oxo-3 -trifluoromethyl-butoxy)-ethoxy]-ethoxy}-3-trifluoromethyl-butane-2-one. The viscosity of this fractionation cut was found to be $5.8 \times 10^{-6}$ $m^2/s$ (5.8 centistokes) at 0° C. and $135.6 \times 10^{-6}$ $m^2/s$ (135.6 centistokes) at −50° C. when measured using an Ubbelohde 545-20 viscometer and a SCHOTT AS350 viscometer timer.

4.43 g of the fractionation cut were heated with 4.46 g of distilled water in a sealed metal (MONEL) tube for 17 hours at 180° C. and then cooled. Analysis of the resulting fluorochemical phase by NMR showed that the phase contained 93.4 mole percent unchanged fractionation cut, indicating surprising stability under relatively extreme conditions.

Example 4

Preparation of $(CF_3)_2CFCF(OCH_3)CF_2(OCF_2CF_2)_2CF_2CF(OCH_3)CF(CF_3)_2$ 40.0 g of the $(CF_3)_2CFC(O)CF_2(OCF_2CF_2)_2CF_2C(O)CF(CF_3)_2$ prepared in Example 3 above, 8.0 g of anhydrous potassium fluoride, 2.9 g of ADOGEN 464 phase transfer catalyst, 19.0 g dimethyl sulfate, and 100 g of anhydrous diglyme were added to a clean, dry 250 mL round bottom flask equipped with a stirrer, a heater, a thermocouple, and a water-cooled condenser. The flask and its contents were heated to 32° C. and held at that temperature for 65 hours. 22 g of water was then added to the flask, and the contents were further heated to 60° C. and held at that temperature for 24 hours. An additional 20 g of water was added to the flask, and the resulting mixture was steam distilled to provide 37.4 g of 85.4 percent by weight purity compound. The structure was confirmed by GCMS.

Example 5

Preparation of $(CF_3)_2CFC(O)CF_2O(CF_2O)_n(CF_2CF_2O)_mCF_2C(O)CF(CF_3)_2$ $FC(O)CF_2O(CF_2O)_n(CF_2CF_2O)_mCF_2C(O)F$ was prepared by the reaction of FOMBLIN Z-DEAL perfluoropolyether di(methyl ester) (commercially available from Solvay-Solexis SpA, Bollate, Italy (Solvay-Solexis, Inc. Thorofare, N.J.)) with fluorine, essentially as described in U.S. Pat. No. 5,399,718 (Costello et. al.), to form a perfluorinated diester that was converted to the corresponding diacyl fluoride by reaction with a catalytic amount of pyridine, essentially as described in U.S. Pat. No. 5,466,877 (Moore). 200 g of 66.0 mole percent pure $FC(O)CF_2O(CF_2O)_n(CF_2CF_2O)_mCF_2C(O)F$ and 181 g anhydrous diglyme were added to a clean, dry 600 mL Parr reactor equipped with a stirrer, a heater, and a thermocouple. The reactor was sealed and evacuated to 0.67 atmosphere (20 inches of mercury) vacuum. The reactor was heated to 75° C., and 42.1 g (0.28 mol) of HFP was added to the reactor over a one hour period. The reactor contents were allowed to stir at 75° C. for an additional 16 hours. The reactor was cooled to room temperature, and excess pressure was vented. The reactor contents were filtered and then added to a separatory funnel to isolate the resulting lower phase. NMR analysis showed 42 mole percent of the desired diketone.

Example 6

Preparation of $CF_3OC_3F_6OCF(CF_3)C(O)CF_2O(C_2F_4O)_m(CF_2O)_nCF_2C(O)CF(CF_3)OC_3F_6OCF_3$ 5 g (0.086 mol) potassium fluoride, 264 g anhydrous diglyme, 7.4 g (49 percent solution in anhydrous diglyme) ADOGEN 464 phase transfer catalyst, 49 g of the perfluoropolyether diacyl fluoride mixture described in Example 1, and 90.5 g (0.27 mol) $CF_3OC_3F_6OCF=CF_2$ were placed into a 600 mL Parr reactor. The reactor was sealed and heated to 75° C. for about 48 hours. The reactor was then cooled, vented, its contents filtered through a sintered glass funnel, and the resulting filtrate separated to provide 115 g of a fluorochemical phase. This phase was then distilled and separated into a number of fractions boiling at temperatures ranging from 34° C. to about 120° C. Two fractions were analyzed by GCMS and found to contain a variety of perfluoropolyether ketones having masses consistent with the following structures: $CF_3OC_3F_6OCF(CF_3)COCF_2OC_2F_5$;

$CF_3OC_3F_6OCF(CF_3)COCF_2OC_2F_4OCF_3$;

$CF_3OC_3F_6OCF(CF_3)COCF_2OC_2F_4OC_2F_4OCF_3$;

$CF_3OC_3F_6OCF(CF_3)COCF_2O(C_2F_4O)_2CF_2OCF_3$;

$CF_3OC_3F_6OCF(CF_3)COCF_2O(C_2F_4O)_3CF_3$;

$CF_3OC_3F_6OCF(CF_3)COCF_2OC_2F_4OCF_2COCF(CF_3)OC_3F_6OCF_3$; and $CF_3OC_3F_6OCF(CF_3)COCF_2O(C_2F_4O)_2CF_2COCF(CF_3)OC_3F_6OCF_3$. IR spectra of the two fractions contained a carbonyl band at about 1794 cm$^{-1}$, consistent with a perfluorinated ketone structure.

Example 7

Preparation of $CF_3OC_3F_6OCF(CF_3)C(O)CF_2O(CF_2O)_n(CF_2CF_2O)_mCF_2C(O)CF(CF_3)OC_3F_6OCF_3$ 5 g (0.086 mol) potassium fluoride, 272 g anhydrous diglyme, 8.9 g (49 percent solution in anhydrous diglyme) ADOGEN 464 phase transfer catalyst, 76 g of the perfluoropolyether diacyl fluoride mixture described in Example 5, and 76 g (0.23 mol) $CF_3OC_3F_6OCF=CF_2$ were placed into a 600 mL Parr reactor. The reactor was sealed and heated to 75° C. for about 48 hours. The reactor was then cooled, vented, its contents filtered through a sintered glass funnel, and the resulting filtrate separated and washed one time with 2-butanone to provide 105 g of a fluorochemical phase (after rotary evaporation of volatile materials). This phase was then distilled under vacuum to remove the lowest boiling materials up to a head temperature of 44° C. at 0.007 atmospheres (5 mm Hg). Distillation residue remaining in the pot weighed 67 g. IR analysis of the residue showed three carbonyl peaks at 1890 cm$^{-1}$ (unreacted perfluoropolyether diacyl fluoride), 1795 cm$^{-1}$, and 1813 cm$^{-1}$. NMR analysis showed that the residue contained about 57 mole percent end groups on the perfluoropolyether chain that were $OCF_2COCF(CF_3)OC_3F_6OCF_3$ and 16 mole percent that were $OCF_2COF$. Other end groups were also present.

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We Claim:

1. A fluorochemical ketone compound consisting of two terminal, branched, independently fluoroalkylcarbonyl or perfluoroalkylcarbonyl groups and an intervening linear perfluoropolyether segment, each of said terminal groups being branched at the carbon atom of the group's fluoroalkyl or perfluoroalkvl moiety that is adjacent to the group's carbonyl moiety, each of said terminal groups optionally comprising at least one catenated heteroatom, and said perfluoropolyether segment consisting essentially of at least one tetrafluoroethyleneoxy moiety and, optionally, at least one difluoromethyleneoxy moiety, said moieties being randomly or non-randomly distributed within said perfluoropolyether segment.

2. The compound of claim 1, wherein said branched terminal groups are independently branched perfluoroalkylcarbonyl groups that optionally contain at least one catenated heteroatom.

3. The compound of claim 2, wherein said branched terminal groups are independently branched perfluoroalkylcarbonyl groups.

4. The compound of claim 1, wherein said perfluoropolyether segment consists essentially of at least one tetrafluoroethyleneoxy moiety and at least one difluoromethyleneoxy moiety.

5. The compound of claim 1, wherein said compound is one of a class that is represented by the following general formula (I):

$$R_f'-C(=O)-[CF_2-O-CF_2CF_2O)_m-(CF_2O)_n-CF_2]-C(=O)-R_f'' \quad (I)$$

wherein Rf' and Rf" are each independently a branched perfluoroalkyl group that optionally contains at least one catenated heteroatom and that optionally comprises a terminal moiety selected from -CF$_2$H, -CFHCF$_3$, and -CF$_2$OCH$_3$; m is an integer of one to 100; n is an integer of zero to 100; and the tetrafluoroethyleneoxy (-CF$_2$CF$_2$O-) and difluoromethyleneoxy (-CF$_2$O-) moieties are randomly or non-randomly distributed.

6. The compound of claim 5, wherein said Rf' and Rf" are each independently branched periluoroalkyl groups that optionally contain at least one catenated heteroatom; said m is an integer of one to 25; and said n is an integer of zero to 25.

7. The compound of claim 6, wherein said Rf' and Rf" are each independently branched perfluoroalkyl groups having from 3 to 6 carbon atoms; said m is an integer of one to 15; and said n is an integer of zero to 15.

8. The compound of claim 1, wherein said compound is selected from $(CF_3)_2CFCOCF_2OCF_2OCF_2COCF(CF_3)_2$ $(CF_3)_2CFCOCF_2OC_2F_4OCF_2COCF(CF_3)_2$ $(CF_3)_2CFCOCF_2OCF_2OCF_2OCF_2COCF(CF_3)_2$ $(CF3)_2CFCOCF2OC2F4OCF2OCF2COCF(CF3)2$ $(CF_3)_2CFCOCF_2OC_2F_4OC_2F_4OCF_2COCF(CF_3)_2$ $(CF_3)_2CFCOCF_2OC_2F_4OCF_2OCF_2OCF_2COCF(CF_3)_2$ $(CF_3)_2CFCOCF_2OCF_2OC_2F_4OCF_2OCF_2COCF(CF_3)_2$ $(CF_3)_2CFCOCF_2OC_2F_4OCF_2OC_2F_4OCF_2COCF(CF_3)_2$ $(CF_3)_2CFCOCF_2OC_2F_4OC_2F_4OCF_2OCF_2COCF(CF_3)_2$ $(CF_3)_2CFCOCF_2OC_2F_4OC_2F_4OC_2F_4OCF_2COCF(CF_3)_2$ $(CF_3)_2CFCOCF_2OC_2F_4OC_2F_4OC_2F_4OC_2F_4OCF_2COCF(CF_3)_2$ $(CF_3)_2CFCOCF_2O(C_2F_4O)_m(CF_2O)_nCF_2COCF(CF_3)_2$, where m is an integer of 1-100 and n is an integer of 0-100

$C_3F_7O(CF_3)CFCOCF_2OCF_2OCF_2COCF(CF_3)OC_3F_7$ $C_3F_7O(CF_3)CFCOCF_2OC_2F_4OCF_2COCF(CF_3)OC_3F_7$ $C_4F_9O(CF_3)CFCOCF_2OCF_2OCF_2COCF(CF_3)OC_4F_9$ $C_3F_7OCF(CF_3)CF_2O(CF_3)CFCOCF_2OC_2F_4OCF_2OCF_2COCF(CF_3)OCF_2CF(CF_3)_7$ $CF_3OC_3F_6O(CF_3)CFCOCF_2OC_2F_4OC_2F_4OCF_2COCF(CF_3)OC_3F_6OCF_3$ $C_3F_7O(CF_3)CFCOCF_2OC_2F_4OCF_2OCF_2OCF_2COCF(CF_3)OC_3F_7$ $H(CF_2)_4O(CF_3)CFCOCF_2OCF_2OC_2F_4OCF_2OCF_2COCF(CF_3)O(CF_2)_4CF_2H$ $HC_2F_4O(CF_3)CFCOCF_2OC_2F_4OCF_2OC_2F_4OCF_2COCF(CF_3)OC_2F_4CF_2H$ $(CF_3)_2CFCOCF_2OC_2F_4OC_2F_4OCF_2OCF_2COCF(CF_3)OC_3F_7$ $C_4F_9O(CF_3)CFCOCF_2OC_2F_4OC_2F_4OC_2F_4OCF_2COCF(CF_3)OC_4F_9$ $C_3F_7O(CF_3)CFCOCF_2OC_2F_4OC_2F_4OC_2F_4OCF_2COCF(CF_3)OC_3F_7$ $CF_3OC_3F_6OCF(CF_3)COCF_2O(C_2F_4O)_m(CF_2O)_nCF_2COCF(CF_3)OC_3F_6OCF_3$, where m is an integer of 1-100 and n is an integer of 0-100

$CF_3OC_3F_6OCF(CF_3)COCF_2OC_2F_4OCF_2COCF(CF_3)OC_3F_6OCF_3$ $CF_3OC_3F_6OCF(CF_3)COCF_2O(C_2F_4O)_2CF_2COCF(CF_3)OC_3F_6OCF_3$ and mixtures thereof.

9. A perfluoroketone compound consisting of two branched, terminal periluoroalkylcarbonyl groups and an intervening linear perfluoropolyether segment, each of said terminal groups being branched at the carbon atom of the group's periluoroalkyl moiety that is adjacent to the group's carbonyl moiety, each of said terminal groups optionally comprising at least one catenated oxygen atom, and said perfluoropolyether segment consisting essentially of at least one tetrafluoroethyleneoxy moiety and at least one difluoromethyleneoxy moiety, said moieties being randomly or non-randomly distributed within said perfluoropolyether segment.

10. A process for removing a contaminant from an article comprising contacting said article with a composition comprising at least one compound of claim 1.

11. A process for preparing a foamed plastic comprising vaporizing a blowing agent mixture in the presence of at least one foamable polymer or the precursors of at least one foamable polymer, said blowing agent mixture comprising at least one compound of claim 1.

12. A process for vapor phase soldering comprising melting solder by immersing at least one component that comprises said solder in a body of fluorochemical liquid vapor that comprises at least one compound of claim 1.

13. A process for transferring heat comprising transferring heat between a heat source and a heat sink through the use of a heat transfer agent comprising at least one compound of claim 1.

14. A process for depositing a coating on a substrate comprising applying to at least a portion of at least one surface of said substrate a composition comprising (a) a solvent composition comprising at least one compound of claim 1; and (b) at least one coating material that is soluble or dispersible in said solvent composition.

15. A process for cutting or abrasive working comprising applying a working fluid to a metal, cermet, or composite workpiece and tool, said working fluid comprising at least one compound of claim 1 and at least one lubricious additive.

16. A polymerization process comprising polymerizing at least one monomer in the presence of at least one polymerization initiator and at least one compound of claim 1.

17. A hydrofluoroether compound produced by (a) reacting at least one fluorochemical ketone compound of claim 1 with at least one fluoride source to form at least one fluorochemical alkoxide; and (b) reacting said fluorochemical alkoxide with at least one alkylating agent to form at least one hydrofluoroether compound.

18. The compound of claim 17, wherein said compound consists of two terminal alkoxy-substituted fluoroalkyl or perfluoroalkyl groups and said intervening linear perfluoropolyether segment of said fluorochemical ketone compound.

19. The compound of claim 18, wherein the alkyl moiety of each said terminal group is independently selected from linear alkyl groups, branched alkyl groups, cyclic alkyl groups, and combinations thereof having from one to 10 carbon atoms.

20. A perfluoropolyether diol produced by reacting at least one fluorochemical ketone compound of claim 1 with at least one reducing agent.

21. A perfluoropolyether diol produced by reacting at least one fluorochemical ketone compound of claim 2 with at least one reducing agent.

22. The diol of claim 20, wherein said diol consists of two terminal hydroxyl-substituted fluoroalkyl or periluoroalkyl groups and said intervening linear perfluoropolyether segment of said fluorochemical ketone compound.

23. A composition comprising at least one fluorochemical ketone compound of claim 1.

24. The composition of claim 23, wherein said moieties are randomly distributed within said perfluoropolyether segment.

* * * * *

UNITED STATES PATENT AND TRADEMARK OFFICE
CERTIFICATE OF CORRECTION

| | | |
|---|---|---|
| PATENT NO. | : 7,385,089 B2 | |
| APPLICATION NO. | : 11/567398 | |
| DATED | : June 10, 2008 | |
| INVENTOR(S) | : Michael G Costello | |

It is certified that error appears in the above-identified patent and that said Letters Patent is hereby corrected as shown below:

Column 4
Line 35; Delete "$(CF_{32}$" and insert -- $(CF_3)_2$ --, therefor.

Column 6
Line 59; After "thereof" insert -- . --.

Column 7
Line 15; Delete "$CH_2$," and insert -- $CF_2$, --, therefor.
Line 23; Delete "CF2OCF==CF2," and insert -- $CF_2OCF==CF_2$, --, therefor.
Line 25; Delete "CF2CF2OCF==CF2," and insert -- $CF_2CF_2OCF==CF_2$, --, therefor.
Line 31 (Approx.); After "thereof" insert -- . --.
Line 47 (Approx.); Delete "thereof," and insert -- thereof; --, therefor.
Line 55 (Approx.); Delete "thereof," and insert -- thereof; --, therefor.

Column 9
Line 9; After "et al.)" insert -- , --.

Column 12
Line 34; Delete "$(CF20)_n$" and insert -- $(CF_2O)_n$ --, therefor.

Column 16
Line 40; Delete "follows:" and insert -- follows. --, therefor.
Line 48 (Approx.); In Claim 1, delete "perfluoroalkvl" and insert
-- perfluoroalkyl --, therefor.

Column 17
Line 4 (Approx.); In Claim 5, delete "$CF_2CF_2$" and insert -- $(CF_2CF_2$ --, therefor.
Line 15 (Approx.); In Claim 6, delete "periluoroalkyl" and insert
-- perfluoroalkyl --, therefor.

Signed and Sealed this
Twelfth Day of April, 2011

David J. Kappos
*Director of the United States Patent and Trademark Office*

CERTIFICATE OF CORRECTION (continued)
U.S. Pat. No. 7,385,089 B2

Line 32 (Approx.); In Claim 8, delete "(CF3)$_2$CFCOCF2OC2F4OCF2OCF2COCF(CF3)2" and insert -- (CF$_3$)$_2$CFCOCF$_2$OC$_2$F$_4$OCF$_2$OCF$_2$COCF(CF$_3$)$_2$ --, therefor.

Line 62 (Approx.); In Claim 8, delete "OCF$_2$COCF(CF$_3$)OCF$_2$CF(CF$_3$)$_7$" and insert -- OCF$_2$COCF(CF$_3$)OCF$_2$CF(CF$_3$)OC$_3$F$_7$ --, therefor.

Column 18

Line 24; In Claim 9, delete "periluoroalkylcarbonyl" and insert -- perfluoroalkylcarbonyl --, therefor.

Line 27; In Claim 9, delete "periluoroalkyl" and insert -- perfluoroalkyl --, therefor.

Column 20

Line 8; In Claim 22, delete "periluoroalkyl" and insert -- perfluoroalkyl --, therefor.